(12) United States Patent
Makaram et al.

(10) Patent No.: US 9,689,836 B2
(45) Date of Patent: Jun. 27, 2017

(54) FUNCTIONALIZED CARBON NANOTUBE SENSORS, METHOD OF MAKING SAME AND USES THEREOF

(71) Applicants: Prashanth Makaram, Burlington, MA (US); Steve Lerner, Carlisle, MA (US)

(72) Inventors: Prashanth Makaram, Burlington, MA (US); Steve Lerner, Carlisle, MA (US)

(73) Assignee: ALPHASZENSZOR, INC, Burlington, MA (US)

( * ) Notice: Subject to any disclaimer, the term of this patent is extended or adjusted under 35 U.S.C. 154(b) by 0 days.

(21) Appl. No.: 15/169,138

(22) Filed: May 31, 2016

(65) Prior Publication Data

US 2016/0356741 A1   Dec. 8, 2016

Related U.S. Application Data

(60) Provisional application No. 62/169,614, filed on Jun. 2, 2015.

(51) Int. Cl.
*H01L 23/04* (2006.01)
*G01N 27/414* (2006.01)

(52) U.S. Cl.
CPC ................... *G01N 27/4146* (2013.01)

(58) Field of Classification Search
CPC .. G01N 27/4146; H01L 21/4817; H01L 23/04
See application file for complete search history.

(56) References Cited

U.S. PATENT DOCUMENTS

| 2004/0136866 A1 | 7/2004 | Pontis et al. |
| 2005/0230822 A1 | 10/2005 | Tran |
| 2006/0115640 A1 | 6/2006 | Yodh et al. |
| 2008/0093226 A1 | 4/2008 | Briman et al. |

(Continued)

FOREIGN PATENT DOCUMENTS

WO   WO2005/019793 A2   3/2005

OTHER PUBLICATIONS

Lee et al., "Soft X-ray Absorption Spectroscopy Studies of the Electronic Structure Recovery of Graphene Oxide upon Chemical Defunctionalization", The Journal of Physical Chemistry C 2012, 116, Sep. 17, 2012, 20591-20599.

(Continued)

*Primary Examiner* — Kyoung Lee
(74) *Attorney, Agent, or Firm* — AKC Patents, LLC (57) ABSTRACT

A carbon nanotube sensor device includes one or more carbon nanotubes and a functionalization layer. An outer surface of the one or more carbon nanotubes is coated with the functionalization layer and the functionalization layer includes a chemical compound that binds to one or more specific analytes. Binding of the one or more specific analytes to the functionalization layer alters an electrical property of the carbon nanotube sensor device and contributes to their detection. The functionalization layer includes a first layer stacked onto an outer surface of the carbon nanotubes, a second layer stacked onto the first layer and a third layer stacked onto the second layer. The first layer enables stacking of a polymer onto the carbon nanotubes. The second layer includes the polymer and the third layer includes the chemical compound that binds to the one or more a specific analytes.

24 Claims, 5 Drawing Sheets

(56) References Cited

U.S. PATENT DOCUMENTS

2010/0176822 A1* 7/2010 Offermans ............. B82Y 15/00
  324/663
2011/0287977 A1  11/2011  Cai et al.
2012/0166095 A1   6/2012  Potyrailo et al.
2012/0206155 A1   8/2012  Wang et al.
2013/0330231 A1  12/2013  Swager et al.
2016/0077047 A1   3/2016  Khamis et al.
2016/0097764 A1   4/2016  Taslim et al.

OTHER PUBLICATIONS

Patil et al., "Graphene Oxide and Functionalized Multi Walled Carbon Nanotubes as Epoxy Curing Agents: A Novel Synthetic Approach to Nanocomposites Containing Active Nanostructured Fillers", RSC Advances, DOI: 10.1039/C4RA09693B, Aug. 31, 2014.

Bilalis, P et al, "Noncovalent functionalization of carbon nanotrubes with polymers", Royal Society of Chemistry advances, 2014, vol. 4, p. 2919-2922.

Peckan, O, et al, "Gelation Mechanisms", Modern Physics letters B, 2012, vol. 26, No. 27; p. 3, p. 7, p. 9, p. 10, p. 20.

* cited by examiner

FUNCTIONALIZED CARBON NANOTUBE SENSORS, METHOD OF MAKING SAME AND USES THEREOF

CROSS REFERENCE TO RELATED CO-PENDING APPLICATIONS

This application claims the benefit of U.S. provisional application Ser. No. 62/169,614 filed on Jun. 2, 2015 and entitled "FUNCTIONALIZED CARBON NANOTUBE SENSORS, METHOD OF MAKING SAME AND USES THEREOF", the contents of which are expressly incorporated herein by reference.

FIELD OF THE INVENTION

The present invention relates generally to the field of carbon nanotube sensor devices. More specifically, the present invention discloses a carbon nanotube sensor device and the method of functionalizing the same in-order to detect at least one analyte.

BACKGROUND OF THE INVENTION

Carbon nanotubes (CNTs) are excellent material for sensors due to their small form factor, high sensitivity, superior electrical properties and flexibility in adding sensitizing (functionalization) layers onto their surface. CNTs are essentially single sheets of graphene rolled into cylinders. They usually possess a single wall, double wall or multiple walls. The typical diameter is 0.4-10 nm and the length may vary from several nanometers to centimeters.

Carbon nanotube sensor devices have found several applications as chemical sensors and can detect analytes in gas phase and liquid phase. CNT based chemical sensors are essentially electrochemical sensors and can be used in either a resistor or a field effect transistor configuration. In order to selectively detect specific analytes the CNT sensors are functionalized.

SUMMARY OF THE INVENTION

In general, in one aspect, the invention features a carbon nanotube sensor device including one or more carbon nanotubes and a functionalization layer. An outer surface of the one or more carbon nanotubes is coated with the functionalization layer and the functionalization layer includes a chemical compound that binds to one or more specific analytes. Binding of the one or more specific analytes to the functionalization layer alters an electrical property of the carbon nanotube sensor device.

Implementations of this aspect of the invention may include one or more of the following features. The functionalization layer comprises a random co-polymer. The random copolymer is stacked onto the carbon nanotubes via π-π bonding interactions, van der Waals interactions, or hydrophobic interactions. The functionalization layer includes a first layer stacked onto an outer surface of the carbon nanotubes, a second layer stacked onto the first layer and comprising the polymer, and a third layer stacked onto the second layer and comprising the chemical compound that binds to the one or more a specific analytes. The first layer enables stacking of a polymer onto the carbon nanotubes. The first layer comprises a polycyclic aromatic compound. The polycyclic aromatic compound comprises one of pyrene, anthracene, pentacene, benzo[a]pyrene, chrysene, coronene, corannulene, naphthacene, phenanthrene, triphenylene, ovalene, benzophenanthrene, perylene, benzo[ghi]peiylene, antanthrene, pentaphene, picene, dibenzo[3,4;9,10]pyrene, benzo[3,4]pyrene, dibenzo[3,4;8,9]pyrene, dibenzo[3,4;6,7]pyrene, dibenzo[1,2;3,4]pyrene naphto[2,3;3,4]pyrene, porphyrin derivatives, or any combination thereof. The polymer comprises one of Poly(methyl methacrylate) (PMMA), poly(aryleneethynylene), poly(phenyleneethynylene) or poly(3-decylthiophene). The polymer wraps partially or completely the outer surface of the carbon nanotubes. The chemical compound that binds with one or more specific analytes comprises one of octyl, ethyl benzyl, or butanol side groups. The binding of the chemical compound with the one or more specific analytes modifies the stacking of the first layer onto the outer surface of the carbon nanotubes and alters the extent of charge transfer between the polymer and the carbon nanotubes and thereby alters carrier density of the carbon nanotubes. The binding of the chemical compound with the one or more specific analytes occurs via π-π bonding interactions, van der Waals interactions, or hydrophobic interactions. The random copolymer comprises a two-component copolymer, and the two-component copolymer comprises a pyrene monomer and a methacrylate monomer.

The two-component copolymer is customized to specifically recognize a specific analyte by tuning an R' sidechain on the pyrene monomer, and/or by tuning an R group on the methacrylate monomer. Altering an R group on the methacrylate monomer customizes the interactions between the polymer and the carbon nanotubes. The two-component polymer is formed by reacting hydroxypyrene with methylmethacrylic acid. One component of the two-component polymer becomes extremely hydrophilic through incorporation of a precursor. The precursor comprises one of hydroxyalkyl, acrylate, or methacrylate groups. The device further includes a field effect transistor (FET) or a resistor and the carbon nanotubes are electrically coupled to the FET or the resistor.

In general, in another aspect, the invention features a method of producing a carbon nanotube sensor device including providing one or more carbon nanotubes, fabricating a sensor device comprising the one or more carbon nanotubes, packaging the sensor device into a semiconductor package, and subsequently, functionalizing the one or more carbon nanotubes by coating an outer surface of the one or more carbon nanotubes with a functionalization layer. The functionalization layer comprises a chemical compound that binds to one or more specific analytes and binding of the one or more specific analytes to the functionalization layer alters an electrical property of the carbon nanotube sensor device.

Implementations of this aspect of the invention may include one or more of the following features. The method further includes rinsing and drying of the functionalized carbon nanotubes and finally sealing of the semiconductor package. The functionalized layer is deposited onto the outer surface of the one or more carbon nanotubes via printing, spin coating, spotting, drop casting, or dip coating. The semiconductor package comprises one of transistor outlines (TO)-header, leadless chip carrier, wafer level packaging, a printed circuit board (PCB) or other substrates. Rinsing of the functionalized carbon nanotubes comprises one of rinsing with a solvent used for dispersion of the polymer, gentle nitrogen flow or flipping the semiconductor package to remove un-attached molecules. Drying of the functionalized carbon nanotubes comprises one of drying in an oven or via a hot plate bake. Sealing of the semiconductor package comprises hermetically attaching a cap onto the semiconductor package via welding.

In general, in another aspect, the invention features a method of producing a carbon nanotube sensor device including providing one or more carbon nanotubes, fabricating a sensor device comprising the one or more carbon nanotubes, functionalizing the one or more carbon nanotubes by coating an outer surface of the one or more carbon nanotubes with a functionalization layer, rinsing and drying of the functionalized carbon nanotubes, packaging the sensor device into a semiconductor package, and sealing of the semiconductor device. The functionalization layer comprises a chemical compound that binds to one or more specific analytes, and binding of the one or more specific analytes to the functionalization layer alters an electrical property of the carbon nanotube sensor device.

In general, in another aspect, the invention features a method of producing a carbon nanotube sensor device including providing one or more carbon nanotubes, functionalizing the one or more carbon nanotubes by coating an outer surface of the one or more carbon nanotubes with a functionalization layer, rinsing and drying of the functionalized carbon nanotubes, fabricating a sensor device comprising the one or more carbon nanotubes, packaging the sensor device into a semiconductor package, and sealing of the semiconductor device. The functionalization layer comprises a chemical compound that binds to one or more specific analytes and binding of the one or more specific analytes to the functionalization layer alters an electrical property of the carbon nanotube sensor device.

BRIEF DESCRIPTION OF THE DRAWINGS

Referring to the figures, wherein like numerals represent like parts throughout the several views.

DETAILED DESCRIPTION OF THE INVENTION

The present invention describes functionalized carbon nanotube devices and methods of making them. The devices include of at least one carbon nanotube, whose surface is non-covalently functionalized in order to detect and/or quantify an analyte or a group of analytes. In some embodiments the functional or recognition layer is a random conjugated polymer. In certain embodiments the surface of the carbon nanotubes is first partially or completely wrapped by the functional copolymers. The polymer is stacked onto the carbon nanotube via π-π interactions. In certain embodiments additional chemical compounds are stacked onto the polymer backboned that are receptive to one or more analytes.

The CNT devices are ideal for usage as sensor systems, in particular for usage in the health and wellness applications. In one example, the CNT device is used to detect disease specific volatile organic compounds (VOC) in breath.

In the following description, the term "sensor" or "sensing element" refers to a sensor that is capable of generating a response when in contact with or proximity to one or more chemical species.

The term "analyte," refers to a substance that is being identified, detected or measured by a sensor, or is identifiable, detectable, or measurable by the sensor. An analyte may be a gas or component of a fluid (e.g., vapor) sample that is sensed by the chemical sensor. Examples of analytes include, without limitation, alcohols, carboxylic acids, aldehydes, ketones, alkanes, alkenes, alkynes, aromatics, nitrogen oxide (e.g., NO, $NO_2$), carbon monoxide, carbon dioxide, volatile organic compounds, water, hydrogen peroxide, sulfur oxides (e.g., $SO_2$), ammonia, $H_2S$, organic acids and inorganic acids, among others (PLEASE ADD/CHECK)

The term "carbon nanotube," (CNT) generally refers to a nanostructure with at least one dimension from at least a nanometer to a hundred nanometers or a micron (1000 nanometers (nm)). Carbon nanotubes refer specifically to hollow tubular structures. CNTs may have various morphologies, including single-walled carbon nanotubes (SWNTs) and multi-walled carbon nanotubes (MWNTs), among others. SWNTs are generally single sheets of graphene rolled into a seamless tube, whereas MWNTs are a concentric arrangement of one or more SWNTs that differ in diameter. Furthermore, CNTs may be individual CNTs or may be a group of CNTs that forms a network of carbon nanotubes.

The present invention provides CNT based sensor devices and methods for chemical sensing that are capable of achieving compact, fast chemical sensing with high sensitivity and specificity. The CNT based sensor devices may include a single sensor or a plurality of sensors arranged in at least one array. Each sensor of a device may be addressable and capable of altered conductivity when in contact with (or proximity to) a given chemical component.

The CNT based sensor devices of the present invention are implemented as a resistor or a field effect transistor (FET). The resistor based sensor device includes a sensing element that is electrically couple to a resistor. The FET based sensor device includes a source, a drain, and a sensing element that is electrically coupled to the source and the drain. The sensing element in the resistor and FET based sensor devices includes one or more CNTs. The CNT's are functionalized so that they are sensitive to one or more analytes or a group of analytes. The CNT's are functionalized by a specific functionalization layer, as will be described below.

The CNT based sensor devices of the present invention may be integrated with various sensing systems. A typical sensing system includes a computer system, a housing, and a gas distribution manifold. The computer system includes a computer processor or other logic. The housing includes an array of individual sensors, and the gas distribution manifold includes a gas flow path that is in communication with the sensor array. The gas flow path brings a gas including one or more analytes in contact with the sensor array. The computer system may be integrated with the sensor housing or external to the sensor housing. In some examples, the computer system is a personal computer or a mobile computing device including smart phones, smart personal assistants or tablets, among others.

Figure 1:
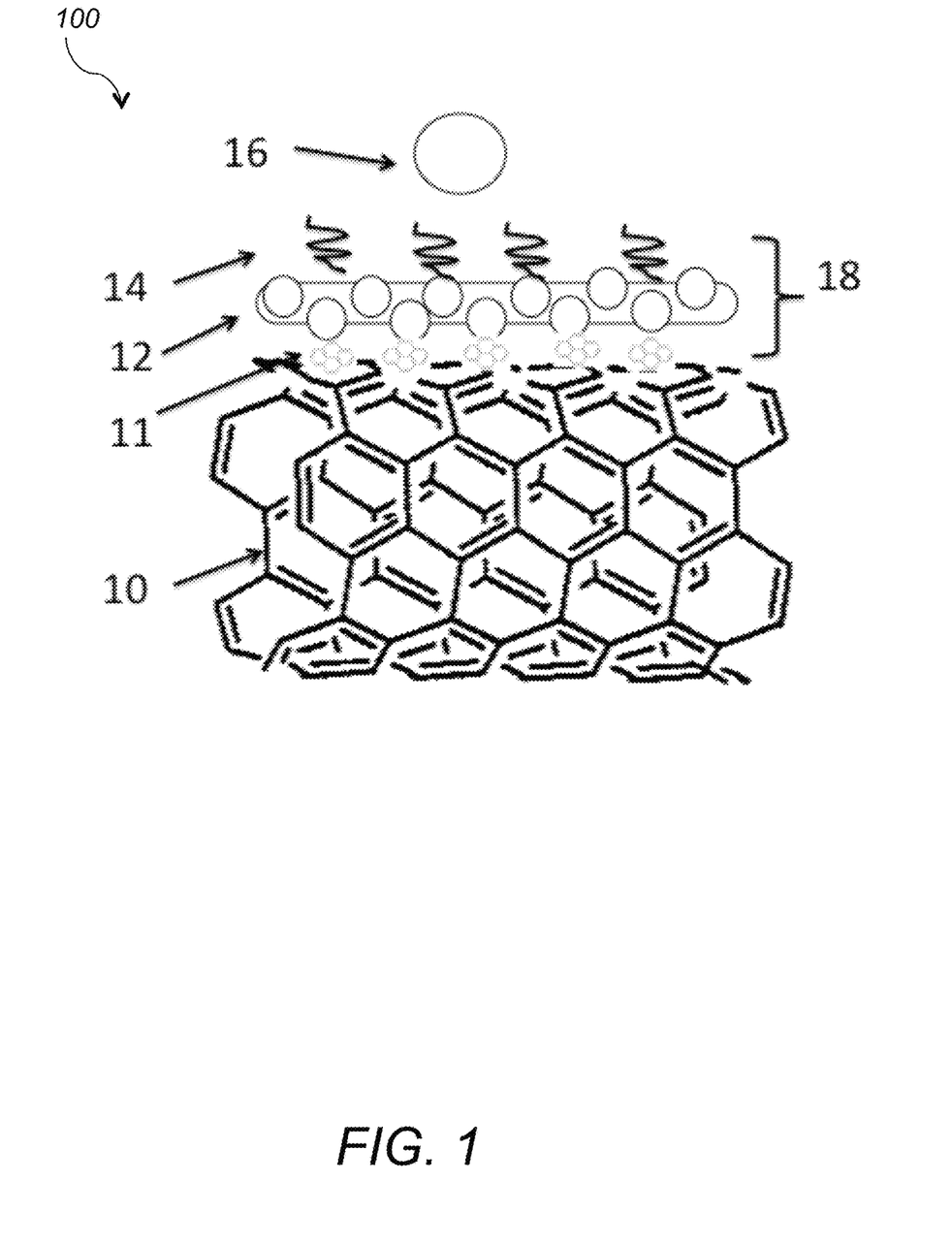
FIG. 1 depicts an embodiment of a carbon nanotube (CNT) sensing element, according to this invention.

Referring now to the invention in more detail, FIG. 1 is an embodiment of a carbon nanotube (CNT) sensing element 100. The sensing element 100 contains one or more carbon nanotubes 10. In some embodiments, the one or more carbon nanotubes 10 are arranged so that they form a network of carbon nanotubes 10. The carbon nanotubes 10 are coated with a recognition or functionalization layer 18 in order to make the CNT more specific or less specific to one or more analytes including ambient conditions such as humidity. In one example, the recognition or functionalization layer 18 includes a random copolymer. The copolymer may contain one or more components. In one embodiment the copolymer includes three component layers: A layer 11 that allows stacking of the polymer onto the nanotubes 10, the polymer backbone 12 and a chemical compound 14 that binds with the analyte of interest 16. In one example, the layer 11 is a polycyclic aromatic group, including pyrene, anthracene, pentacene, benzo[a]pyrene, chrysene, coronene, corannulene, naphthacene, phenanthrene, triphenylene, ovalene, benzophenanthrene, perylene, benzo[ghi]peiylene, antanthrene, pentaphene, picene, dibenzo[3,4;9,10]pyrene, benzo[3,4]pyrene, dibenzo[3,4;8,9]pyrene, dibenzo[3,4;6,7]pyrene, dibenzo[1,2;3,4]pyrene, naphto[2,3;3,4]pyrene, porphyrin derivatives, or any combination thereof. In preferred embodiments the layer 11 is either a pyrene moiety or a linear chain of aromatic rings. Layer 11 allows stacking of the polymer 12 onto the carbon nanotubes 10 through $\pi$-$\pi$ interactions. The incorporation of multiple compounds of layer 11 within the random copolymer mediates multivalent interactions enabling the polymer to strongly bind with the carbon nanotubes 10. The strong bond between the polymer 12 and carbon nanotubes 10 enables strong charge transfer interactions between the polymer and the carbon nanotubes and has a pronounced effect on the carrier density of the conducting or semiconducting devices that include the carbon nanotubes. Notably, the $\pi$-$\pi$ stacking interactions within hydrophobic domains are stable even upon exposure to moisture. The copolymer 12 may be one of Poly(methyl methacrylate) (PMMA), poly(aryleneethynylene), poly(phenyleneethynylene) and poly(3-decylthiophene), among others. The copolymer 12 may be stacked on the carbon nanotube 10 through a $\pi$-$\pi$ interaction, a van der Waals interaction, or a hydrophobic interaction. In one example, the polymer 12 is a Poly(methyl methacrylate) (PMMA) that wraps partially or completely the nanotube through $\pi$-$\pi$ interactions. The layer 11 is functionalized to include a pendant chain 14 to recognize specific analytes. For example the pyrene moieties or linear aromatic chains 11 are modified to bear octyl, ethyl benzyl, or butanol side groups. Binding of the analyte 16 to these recognition elements 14 modifies the $\pi$-$\pi$ stacking interactions between layer 11 and the carbon nanotube 10 sidewalls, thereby altering the extent of charge transfer between the polymer 12 side chain and the carbon nanotube 10. Modifying the charge transfer interaction between the nanotube 10 and the polymer 12 in essence is analogous to applying of a gate voltage to a semiconducting device that includes the carbon nanotubes and substantially alters the carrier density within the semiconducting channels of nanotube transistors. Multiple binding events across the polymer 12 chain have an "avalanche" or cooperative effect, modifying the conformation of the polymer stacked onto the nanotube 10, which is reflected in a substantial increase or decrease in the current at a specified bias voltage as the electron or hole density is modulated. In other embodiments, the recognition element 14 is incorporated within the polymer backbone 12 separate from the polycyclic aromatic group layer 11. Binding of analyte 16 species to the recognition elements 14 occurs through a $\pi$-$\pi$ interaction, a van der Waals interaction, or a hydrophobic interaction. In preferred embodiments the binding of the analyte 16 species to recognition element 14 is primarily mediated through non-covalent van der Waals' interactions and is readily reversible upon a mild thermal (or voltage-induced) annealing step.

Figure 2:
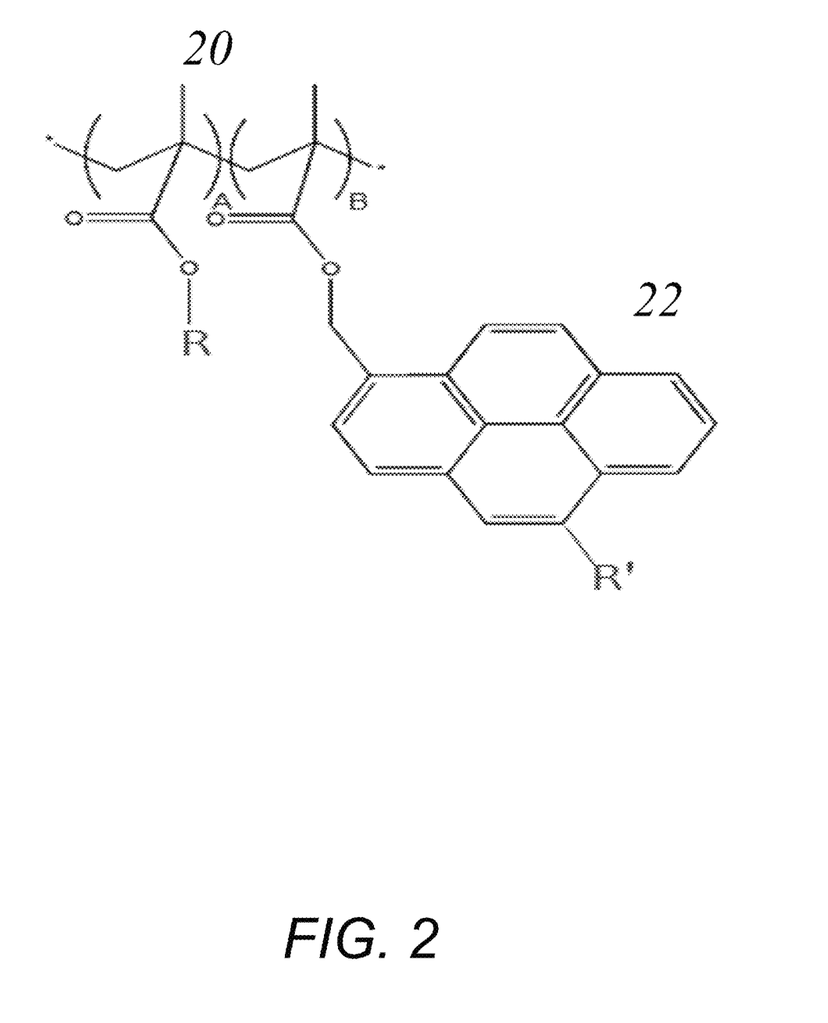
FIG. 2 depicts an example of a simple two-component random co-polymer used in the CNT sensing element of FIG. 1.

FIG. 2 shows an example of a simple two-component random co-polymer that can be customized to specifically recognize a certain analyte based on tuning the R' sidechain on the pyrene 22 monomer. For instance, grafting a long aliphatic chain allows preferential binding of volatile organic compounds (VOC's) such as hexane and octane, whereas grafting an aromatic group allows recognition of ethyl benzene and analogous aromatic analytes. In some embodiments, the pyrene moieties 22 stack onto the conjugated sidewalls of the carbon nanotubes 10 via $\pi$-$\pi$ interactions, whereas the methacrylate groups 20 constitute the polymer backbone. Altering the R group on the methacrylate monomer 20 can further mediate the polymer-nanotube interactions. For instance, incorporation of n-octylmethacrylate enables recognition of octane vapor along the polymer backbone. In certain embodiments, R and R' can be designed to selectively bind different analyte components of interest. R and R' may be long aliphatic chains, or aromatic groups, among others. In one example, R=octyl and R'=ethylbenzyl allows simultaneous binding of two different analytes and has very different effects on modulating the current in the nanotube channels. This enables quantification of concentrations of both analytes upon application of the appropriate multivariate statistical algorithms. In certain embodiments the R or R' group interacts with multiple analytes simultaneously. In other embodiments there are 'n' number of sidechain R'' on the polymer backbone to detect 'n' number of analytes. The pyrene-methylmethacrylate monomer depicted in FIG. 2 can be derived from a simple coupling reaction between hydroxypyrene and methylmethacrylic acid. The ratio of A and B in the random copolymer can be varied to optimize the response and sensitivity to different analytes. For increased sensitivity, a greater number of polyaromatic groups bearing recognition elements are incorporated within the polymer till such point that solubility and packing of pyrene moieties on the nanotubes becomes a limiting factor.

In other embodiments, one component of the polymer 20 is rendered extremely hydrophilic through incorporation of a precursor such as hydroxyethylmethacrylate (HEMA). This gives rise to distinctive hydrophilic and hydrophobic domains within the polymer wrapped around the nanotube 10 and allows for increased local concentrations of non-polar analytes in the hydrophobic domains and essentially enables their nanoscale separation from moisture. In one example, R=$CH_2CH_2OH$ and R'=n-octyl and the hydroxylated part absorbs moisture through hydrogen bonding interactions till saturation, whereas the hydrophobic moiety is directly $\pi$-$\pi$ stacked onto nanotube 10 sidewalls and remains impervious to moisture but responds to binding of non-polar analytes such as octane. The precursors may be hydroxyalkyl, acrylate, or methacrylate groups.

The random copolymer in the various embodiments described above can be prepared through a single one-pot polymerization reaction from the starting precursors and is processable in solvents such as tetrahydrofuran, chloroform, chlorobenzene, water, acetic acid, acetone, acetonitrile, aniline, benzene, benzonitrile, benzyl alcohol, bromobenzene, bromoform, 1-butanol, 2-butanol, carbon disulfide, carbon tetrachloride, cyclohexane, cyclohexanol, decalin, dibromethane, diethylene glycol, diethylene glycol ethers, diethyl ether, diglyme, dimethoxymethane, N,N-dimethylformamide, ethanol, ethylamine, ethylbenzene, ethylene glycol ethers, ethylene glycol, ethylene oxide, formaldehyde, formic acid, glycerol, heptane, hexane, iodobenzene, mesitylene, methanol, methoxybenzene, methylamine, methylene bromide, methylene chloride, methylpyridine, morpholine, naphthalene, nitrobenzene, nitromethane, octane, pentane, pentyl alcohol, phenol, 1-propanol, 2-propanol, pyridine, pyrrole, pyrrolidine, quinoline, 1,1,2,2-tetrachloroethane, tetrachloroethylene, tetrahydrofuran, tetrahydropyran, tetralin, tetramethylethylenediamine, thiophene, toluene, 1,2,4-trichlorobenzene, 1,1,1-trichloroethane, 1,1,2-trichloroethane, trichloroethylene, triethylamine, triethylene glycol dimethyl ether, 1,3,5-trimethylbenzene, m-xylene, o-xylene, p-xylene, 1,2-dichlorobenzene, 1,3-dichlorobenzene, or 1,4-dichlorobenzene, among others.

Figure 3A:
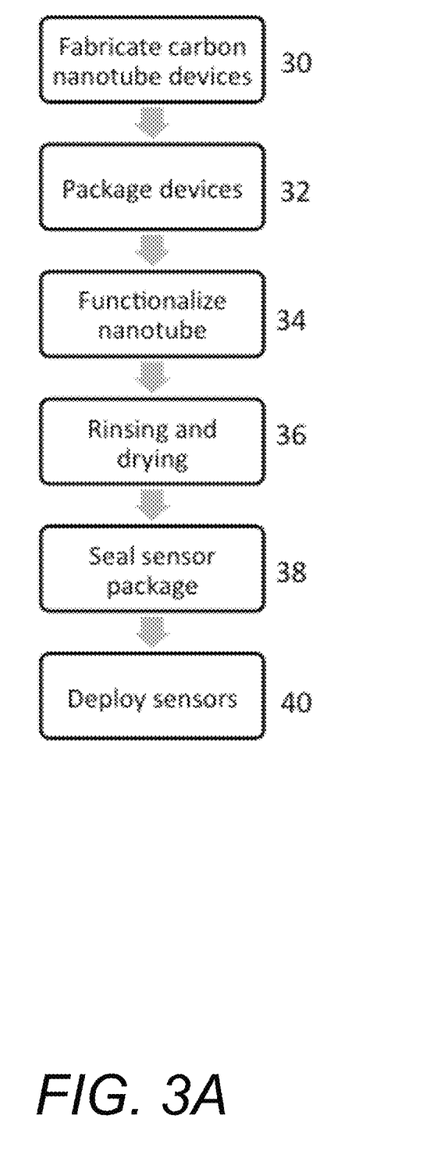
FIG. 3A is a process flow diagram where the functionalization of the carbon nanotube is carried out after the carbon nanotube devices have been fabricated and packaged into a semiconductor package.
Figure 3B:
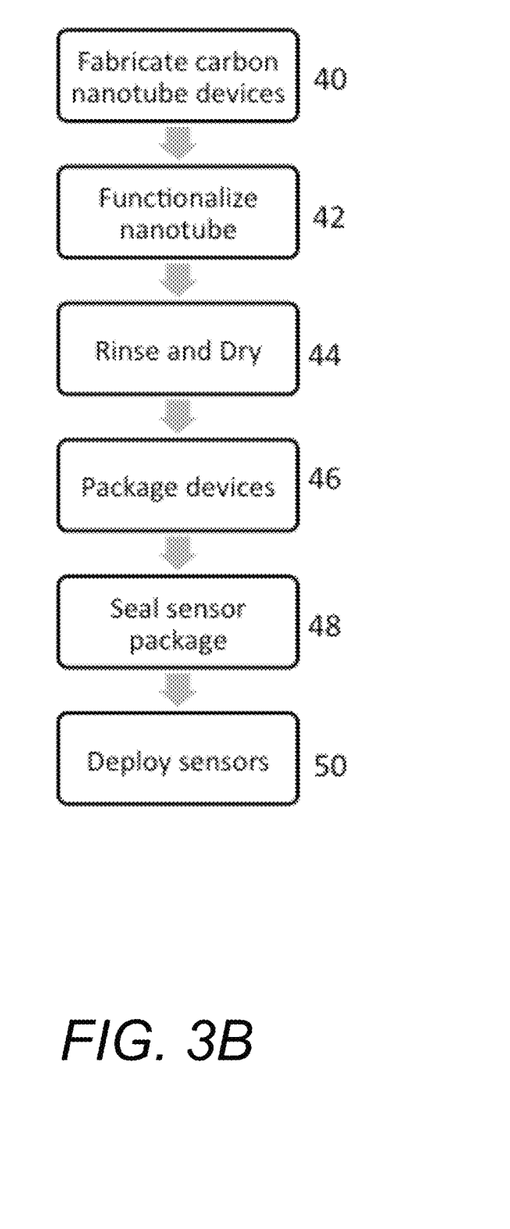
FIG. 3B is a process flow diagram where the functionalization of the carbon nanotube is carried out after the carbon nanotube devices have been fabricated but before they are packaged into a semiconductor package.
Figure 3C:
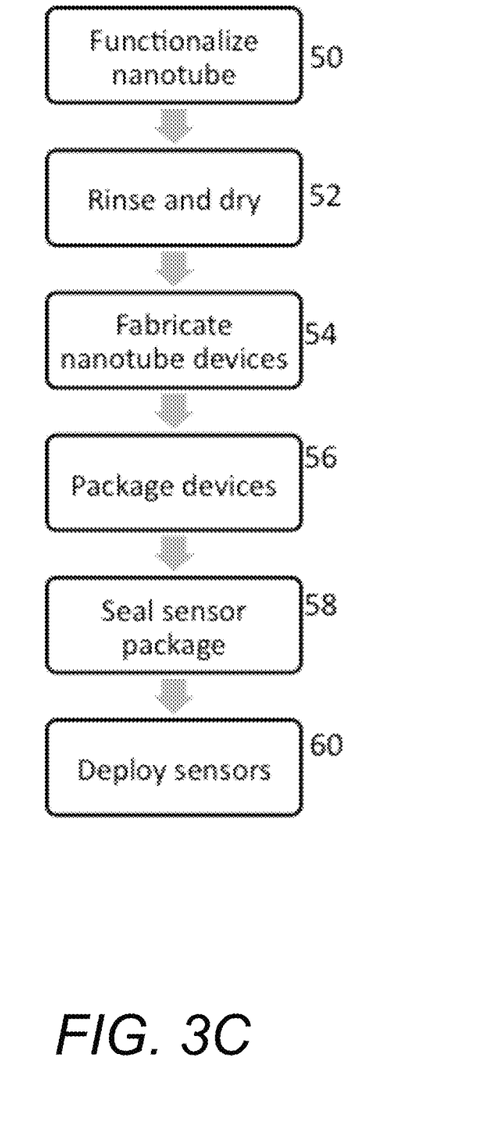
FIG. 3C is a process flow diagram where the functionalization of the carbon nanotube is carried out before the carbon nanotube devices have been fabricated.

FIGS. 3a, 3b and 3c depict the functionalization flow according to certain embodiments of the invention. FIG. 3a depicts a flow according to certain embodiments where the functionalization of the carbon nanotube is carried out after the carbon nanotube devices have been fabricated (30) and packaged into a semiconductor package (TO-header, leadless chip carrier, wafer level packaging etc.), a printed circuit board (PCB) or other similar substrates (32). The conjugated polymer functionalization (34) is then deposited using techniques including but not restricted to printing, spin coating, spotting, drop casting, dip coating, among others. Rinsing and drying steps 36 are incorporated after the functionalization step 34. This may include rinsing with the same solvent used for dispersion of the polymer, gentle nitrogen flow or flipping the chip to remove un-attached molecules and oven or hot plate bake. The package is then sealed 38 as per requirements of the application. For example resistance or laser welding may be carried out to hermetically attach a tin cap onto a TO header package. The sensor 40 is now ready for further characterization or deployment.

FIG. 3b depicts flow according to certain embodiments where the functionalization 42 of the carbon nanotube is carried out after the carbon nanotube devices have been fabricated 40 and but before it is packaged 46 into semiconductor package (TO-header, leadless chip carrier, wafer level packaging etc.), a printed circuit board (PCB) or other similar substrates. The copolymer functionalization 42 is deposited using techniques including but not restricted to printing, spin coating, spotting, drop casting, or dip coating, among others. Rinsing and drying steps 44 are incorporated after functionalization 42. These steps may include rinsing with the same solvent used for dispersion of the polymer, gentle nitrogen flow or flipping the chip to remove un-attached molecules followed by an oven or hot plate bake. The package may then be sealed 48 as per requirements of the application. For example resistance or laser welding may be carried out to hermetically attach a tin cap onto a TO header package. The sensor 50 is now ready for further characterization or deployment.

FIG. 3c depicts flow according to certain embodiments where the functionalization 50 of the carbon nanotube is carried out before the carbon nanotube devices have been fabricated 54. The nanotubes are mixed with the copolymer in the same solvent or the nanotube are deposited first followed by deposition of the polymer. The conjugated polymer functionalization and nanotubes are deposited using techniques including but not restricted to printing, spin coating, spotting, drop casting, dip coating, among others. This may be done on bare substrates or pre-fabricated electrodes. In the former case the device is fabricated 54 after functionalization has been deposited. Rinsing and drying steps 52 may be incorporated after functionalization 50. This may include rinsing with the same solvent used for dispersion of the polymer, gentle nitrogen flow or flipping the chip to remove un-attached molecules and oven or hot plate bake. The nanotube devices are packaged 56 into semiconductor package (TO-header, leadless chip carrier, wafer level packaging etc.), a printed circuit board (PCB) or other similar substrates. The package may then be sealed 58 as per requirements of the application. For example resistance or laser welding may be carried out to hermetically attach a tin cap onto a TO header package. The sensor 60 is now ready for further characterization or deployment.

Several embodiments of the present invention have been described. Nevertheless, it will be understood that various modifications may be made without departing from the spirit and scope of the invention. Accordingly, other embodiments are within the scope of the following claims.

What is claimed is:

1. A carbon nanotube sensor device comprising:
   one or more carbon nanotubes;
   a functionalization layer, wherein an outer surface of the one or more carbon nanotubes is coated with the functionalization layer and wherein the functionalization layer comprises a chemical compound that binds to one or more specific analytes;
   wherein binding of the one or more specific analytes to the functionalization layer alters an electrical property of the carbon nanotube sensor device;
   wherein the functionalization layer comprises a random co-polymer; and
   wherein the random copolymer is stacked onto the carbon nanotubes via π-π bonding interactions, van der Waals interactions, or a hydrophobic interactions.

2. The device of claim 1, wherein the random copolymer comprises a two-component copolymer, and wherein the two-component copolymer comprises a pyrene monomer and a methacrylate monomer.

3. The device of claim 2, wherein the two-component copolymer is customized to specifically recognize a specific analyte by tuning an R' sidechain on the pyrene monomer, and/or by tuning an R group on the methacrylate monomer.

4. The device of claim 2, wherein altering an R group on the methacrylate monomer customizes the interactions between the polymer and the carbon nanotubes.

5. The device of claim 2, wherein the two-component polymer is formed by reacting hydroxypyrene with methylmethacrylic acid.

6. The device of claim 2, wherein one component of the two-component polymer becomes extremely hydrophilic through incorporation of a precursor.

7. The device of claim 6, wherein the precursor comprises one of hydroxyalkyl, acrylate, or methacrylate groups.

8. The device of claim 1, further comprising a field effect transistor (FET) or a resistor and wherein the carbon nanotubes are electrically coupled to the FET or the resistor.

9. A carbon nanotube sensor device comprising:
   one or more carbon nanotubes:
   a functionalization layer, wherein an outer surface of the one or more carbon nanotubes is coated with the functionalization layer and wherein the functionalization layer comprises a chemical compound that binds to one or more specific analytes;

wherein binding of the one or more specific analytes to the functionalization layer alters an electrical property of the carbon nanotube sensor device; and wherein the functionalization layer comprises:
a first layer stacked onto an outer surface of the carbon nanotubes, wherein the first layer enables stacking of a polymer onto the carbon nanotubes;
a second layer stacked onto the first layer and comprising the polymer; and
a third layer stacked onto the second layer and comprising the chemical compound that binds to the one or more a specific analytes.

10. The device of claim 9, wherein the first layer comprises a polycyclic aromatic compound.

11. The device of claim 10, wherein the polycyclic aromatic compound comprises one of pyrene, anthracene, pentacene, benzo[a]pyrene, chrysene, coronene, corannulene, naphthacene, phenanthrene, triphenylene, ovalene, benzophenanthrene, perylene, benzo[ghi]peiylene, antanthrene, pentaphene, picene, dibenzo[3,4;9,10]pyrene, benzo[3,4]pyrene, dibenzo[3,4;8,9]pyrene, dibenzo[3,4;6,7]pyrene, dibenzo[1,2;3,4]pyrene, naphto[2,3;3,4]pyrene, porphyrin derivatives, or any combination thereof.

12. The device of claim 9, wherein the polymer comprises one of Poly(methyl methacrylate) (PMMA), poly(aryleneethynylene), poly(phenyleneethynylene) or poly(3-decylthiophene).

13. The device of claim 9, wherein the polymer wraps partially or completely the outer surface of the carbon nanotubes.

14. The device of claim 9, wherein the chemical compound that binds with one or more specific analytes comprises one of octyl, ethyl benzyl, or butanol side groups.

15. The device of claim 9, wherein binding of the chemical compound with the one or more specific analytes modifies the stacking of the first layer onto the outer surface of the carbon nanotubes and alters the extent of charge transfer between the polymer and the carbon nanotubes and thereby alters carrier density of the carbon nanotubes.

16. The device of claim 9, wherein binding of the chemical compound with the one or more specific analytes occurs via π-πbonding interactions, van der Waals interactions, or a hydrophobic interactions.

17. A method of producing a carbon nanotube sensor device comprising:
providing one or more carbon nanotubes;
fabricating a sensor device comprising the one or more carbon nanotubes;
packaging the sensor device into a semiconductor package;
subsequently, functionalizing the one or more carbon nanotubes by coating an outer surface of the one or more carbon nanotubes with a functionalization layer and
wherein the functionalization layer comprises a chemical compound that binds to one or more specific analytes; and
wherein binding of the one or more specific analytes to the functionalization layer alters an electrical property of the carbon nanotube sensor device.

18. The method of claim 17, further comprising rinsing and drying of the functionalized carbon nanotubes and finally sealing of the semiconductor package.

19. The method of claim 17, wherein the functionalized layer is deposited onto the outer surface of the one or more carbon nanotubes via printing, spin coating, spotting, drop casting, or dip coating.

20. The method of claim 17, wherein the semiconductor package comprises one of transistor outlines(TO)-header, leadless chip carrier, wafer level packaging, a printed circuit board (PCB) or other substrates.

21. The method of claim 18, wherein rinsing of the functionalized carbon nanotubes comprises one of rinsing with a solvent used for dispersion of the polymer, gentle nitrogen flow or flipping the semiconductor package to remove un-attached molecules.

22. The method of claim 18, wherein drying of the functionalized carbon nanotubes comprises one of drying in an oven or via a hot plate bake.

23. The method of claim 18, wherein sealing of the semiconductor package comprises hermetically attaching a cap onto the semiconductor package via welding.

24. A method of producing a carbon nanotube sensor device comprising:
providing one or more carbon nanotubes;
functionalizing the one or more carbon nanotubes by coating an outer surface of the one or more carbon nanotubes with a functionalization layer and wherein the functionalization layer comprises a chemical compound that binds to one or more specific analytes;
rinsing and drying of the functionalized carbon nanotubes;
fabricating a sensor device comprising the one or more carbon nanotubes;
packaging the sensor device into a semiconductor package;
sealing of the semiconductor device; and
wherein binding of the one or more specific analytes to the functionalization layer alters an electrical property of the carbon nanotube sensor device.

* * * * *